United States Patent [19]
Yamamoto et al.

[11] Patent Number: 5,916,781
[45] Date of Patent: Jun. 29, 1999

[54] METHOD FOR PRODUCING D-TRYPTOPHAN

[75] Inventors: Hiroaki Yamamoto; Kazuya Mitsuhashi; Akinobu Matsuyama, all of Ibaraki; Fusao Tomita, Hokkaido, all of Japan

[73] Assignee: Daicel Chemical Industries, Ltd., Japan

[21] Appl. No.: 09/005,110

[22] Filed: Jan. 9, 1998

[30] Foreign Application Priority Data

| Jan. 9, 1997 | [JP] | Japan | 9-002228 |
| May 27, 1997 | [JP] | Japan | 9-136267 |
| Dec. 1, 1997 | [JP] | Japan | 9-329792 |

[51] Int. Cl.$^6$ ............ C12P 13/22; C12P 41/00
[52] U.S. Cl. ............ 435/108; 435/170; 435/252.3; 435/280; 435/320.1
[58] Field of Search ............ 435/108, 280, 435/170, 252.3, 320.1

[56] References Cited

U.S. PATENT DOCUMENTS

| 4,335,209 | 6/1982 | Asai et al. | 435/108 |
| 4,481,362 | 11/1984 | Nakai et al. | 434/280 |
| 4,497,957 | 2/1985 | Asai et al. | 548/496 |

FOREIGN PATENT DOCUMENTS

| 0 043 211 A2 | 6/1982 | European Pat. Off. . | |
| A-Sho 51-6235 | 2/1976 | Japan . | |
| A-Hei 1-256379 | 10/1989 | Japan . | |
| 2 151 634 | 7/1985 | United Kingdom . | |

OTHER PUBLICATIONS

Deeley et al., "Nucleotide Sequence of the Structural Gene for Tryptophanase of *Escherichia coli* K–12", J. of Bacteriol., 147:387–796, 1981.

Kawasaki et al., "Cloning and characterization of a tryptophanase gene from *Enterobacter aerogenes* SM–18", J. of General Microbiology, 139:3275–3281, 1993.

Kawasaki et al., "Enzymatic Synthesis of L–Tryptophan by *Enterobacter aerogenes* Tryptophanase Highly Expressed in *Escherichia coli*, and some Properties of the Purified Enzyme", Biosci. Biotech. Biochem, 59:1938–1943, 1995.

"Enzyme Nomenclature, 1992", Academic Press, Inc., 1992, p. 469.

Yoshida et al., "Purification, Crystallization and Properties of Tryptophanase from *Proteus rettgeri*", Arg. Biol. Chem., 38:2065–2072, 1974.

*Primary Examiner*—Herbert J. Lilling
*Attorney, Agent, or Firm*—Fish & Richardson P.C.

[57] ABSTRACT

The method for producing D-tryptophan with high optical purity and high yield is provided, which comprises contacting a mixture of D,L-tryptophan with organisms which produce tryptophanase to degrade L-tryptophan selectively, thereby increasing the content of D-tryptophan in D,L-tryptophan.

15 Claims, 1 Drawing Sheet

METHOD FOR PRODUCING D-TRYPTOPHAN

FIELD OF THE INVENTION

This invention relates to a method for producing D-tryptophan which comprises selectively degrading L-tryptophan in a D,L-tryptophan mixture to thereby increase the content of D-tryptophan.

BACKGROUND OF THE INVENTION

A known method of producing D-tryptophan comprises contacting D,L-indolyl methylhydantoin with microorganisms capable of selectively hydrolyzing D-indolyl methylhydantoin into N-carbamoyl-D-tryptophan to synthesize N-carbamoyl-D-tryptophan and hydrolyzing the resulting N-carbamoyl-D-tryptophan into D-tryptophan chemically with nitrous acid or the like or by using microorganisms (Hydantoinase method, JP-A-Sho 61-17791).

It is also known to produce D-tryptophan by contacting D,L-tryptophanamide with microorganisms or an enzyme, which are capable of producing D-tryptophan to selectively hydrolyze D-tryptophanamide, (D-Amidase method, JP-B-Hei 8-22228), and by selectively degrading D,L-tryptophanamide L-tryptophanamide and chemically hydrolyzing the remaining D-tryptophanamide (L-Amidase method, JP-A-Sho 57-13000).

In addition, other methods for producing D-tryptophan includes the method in which D-tryptophan is produced from indole pyruvate and D-alanine as an amino group donor by the action of D-amino acid transaminase (Transaminase method, JP-B-Hei 7-85718), the method which comprises contacting N-acetyl-D,L-tryptophan with L-aminoacylase to selectively deacetylate N-acetyl-L-tryptophan and chemically deacetylating the remaining N-acetyl-D-tryptophan (L-aminoacylase method, Methods in Enzymology 3, 554–570, (1957)), the method which comprises contacting N-acetyl-D,L-tryptophan with D-aminoacylase to selectively deacylate N-acetyl-D-tryptophan (D-aminoacylase method, JP-B-Hei 01-29560), and the method which comprises converting D-tryptophan in D,L-tryptophan selectively into N-acetyl-D-tryptophan with D-amino acid acetyltransferase to separate D-tryptophan from L-tryptophan and chemically hydrolyzing the resulting N-acetyl-D-tryptophan (Acetyltransferase method, JP-A-Sho 60-251892).

In view of industrial production of D-tryptophan, these methods have such disadvantages as expensiveness of the substrates, the complicated reaction procedures, the low yield, and the low optical purity.

SUMMARY OF THE INVENTION

As a result of intensive investigation to provide an industrially useful method for producing D-tryptophan, the present inventors have found that the content of D-tryptophan was increased by treating a mixture of D-tryptophan and, L-tryptophan such as D,L-tryptophan with tryptophanase-producing microorganisms to selectively degrade L-tryptophan in D,L-tryptophan, which made it possible to produce D-tryptophan with high optical purity and high yield.

Namely, this invention relates to a method for producing D-tryptophan which comprises contacting a mixture of D,L-tryptophan with tryptophanase to selectively degrade L-tryptophan in the D,L-tryptophan mixture and more specifically to, (1) a method for producing D-tryptophan which comprises contacting a mixture of D,L-tryptophan with tryptophanase, tryptophanase-producing microorganisms, or their treated products to selectively degrade L-tryptophan, thereby increasing the content of D-tryptophan in the D,L-tryptophan mixture.

Preferably, this invention relates to (2) the method as described in (1) above, wherein said tryptophanase is derived from a microorganism belonging to the genus Aeromonas, Enterobacter, Escherichia, Morganella, Paenibacillus, Proteus, Sphaerophorus, Symbiobacterium, or Vibrio, and more preferably, (3) the method as described in (2) above, wherein said tryptophanase is derived from *Aeromonas hydrophila, Enterobacter aerogenes, Escherichia coli, Morganella morganii subsp. morganii, Paenibacillus alvei, Proteus vulgaris, Sphaerophorus funduliformis,* or *Symbiobacterium thermophilum.*

This invention also relates to (4) the method as described in (1) above, wherein said mixture of D,L-tryptophan is contacted with a microorganism belonging to the genus Achromobacter, Aeromonas, Agrobacterium, Alcaligenes, Bacteroides, Cellulomonas, Citrobacter, Clostridium, Corynebacterium, Enterobacter, Erwinia, Escherichia, Morganella, Fusobacterium, Klebsiella, Kluyvera, Morganella, Nocardia, Paenibacillus, Pantoea, Pasteurella, Peptostreptococcus, Pichia, Propionibacterium, Proteus, Providencia, Pseudomonas, Salmonella, Serratia, Sphaerophorus, Symbiobacterium, Vibrio, or Xanthomonas, or their treated products, and, preferably, relates to (5) the method as described in (4) above, wherein said microorganism is *Achromobacter liquidum, Aeromonas hydrophila, Aeromonas hydrophila subsp. hydrophila, Agrobacterium tumefasciens, Alcaligenes faecalis, Bacteroides fragilis, Citrobactert freundii, Clostridium felsineum, Corynebacterium ammoniagenes, Enterobacter aerogenes, Enterobacter cloacae, Erwinia carotovora, Escherichia coli, Fusobacterium varium, Klebsiella oxytoca, Klebsiella planticola, Klebsiella pneumoniae, Kluyvera ascorbata, Morganella morganii subsp. morganii, Nocardia asteroides, Paenibacillus alvei, Pantoea agglomerans, Pantoea ananas, Pasteurella multocida, Peptostreptococcus asaccharolyticus, Pichia anomala, Propionibacterium acnes, Proteus inconstans, Proteus mirabilis, Proteus vulgaris, Providencia rettgeri, Pseudomonas putida, Salmonella choleraesuis subsp. choleraesuis, Serratia grimesii, Sphaerophorus funduliformis, Symbiobacterium thermophilum, Vibrio harveyi, Vibrio cholerae,* or *Xanthomonas campestris.*

This invention further relates to, (6) the method as described in (2) above, wherein said mixture of D,L-tryptophan is contacted with transformants in which a tryptophanase gene has been introduced, or their treated products, and preferably to, (7) the method as described in (6) above, wherein said tryptophanase gene is derived from a microorganism belonging to the genus Alcaligenes, Enterobacter, Escherichia, Proteus, Providencia, or Symbiobacterium, and more preferably to, (8) the method as described in (7) above, wherein said tryptophanase gene is derived from *Alcaligenes faecalis, Enterobacter aerogenes, Escherichia coli, Proteus inconstans, Proteus vulgaris, Providencia rettgeri,* or *Symbiobacterium thermophilum.*

In addition, this invention relates to, (9) the method as described in (2), (4), and (6) above, wherein a microorganism grown in a culture medium containing L-tryptophan is used.

This invention further relates to,

(10) the method as described in (1) above, which further comprises adding in a reaction mixture a surfactant, a nonaqueous solvent which dissolves indole easily, or a water-insoluble resin capable of binding to indole, and preferably to,

(11) the method as described in (10) above, wherein said surfactant is Sorpol W-200 or Nonion NS230, said resin capable of binding to indole is Amberlite XAD-7, and the organic solvent is toluene or hexane.

Furthermore, this invention relates to,

(12) the method as described in (1) above, which further comprises adding a microorganism capable of degrading pyruvic acid to the reaction mixture, and preferably to,

(13) the method as described in (12) above, wherein said microorganism capable of degrading pyruvic acid is a microorganism belonging to the genus Corynebacterium.

DETAILED DESCRIPTION OF THE INVENTION

Figure 1:
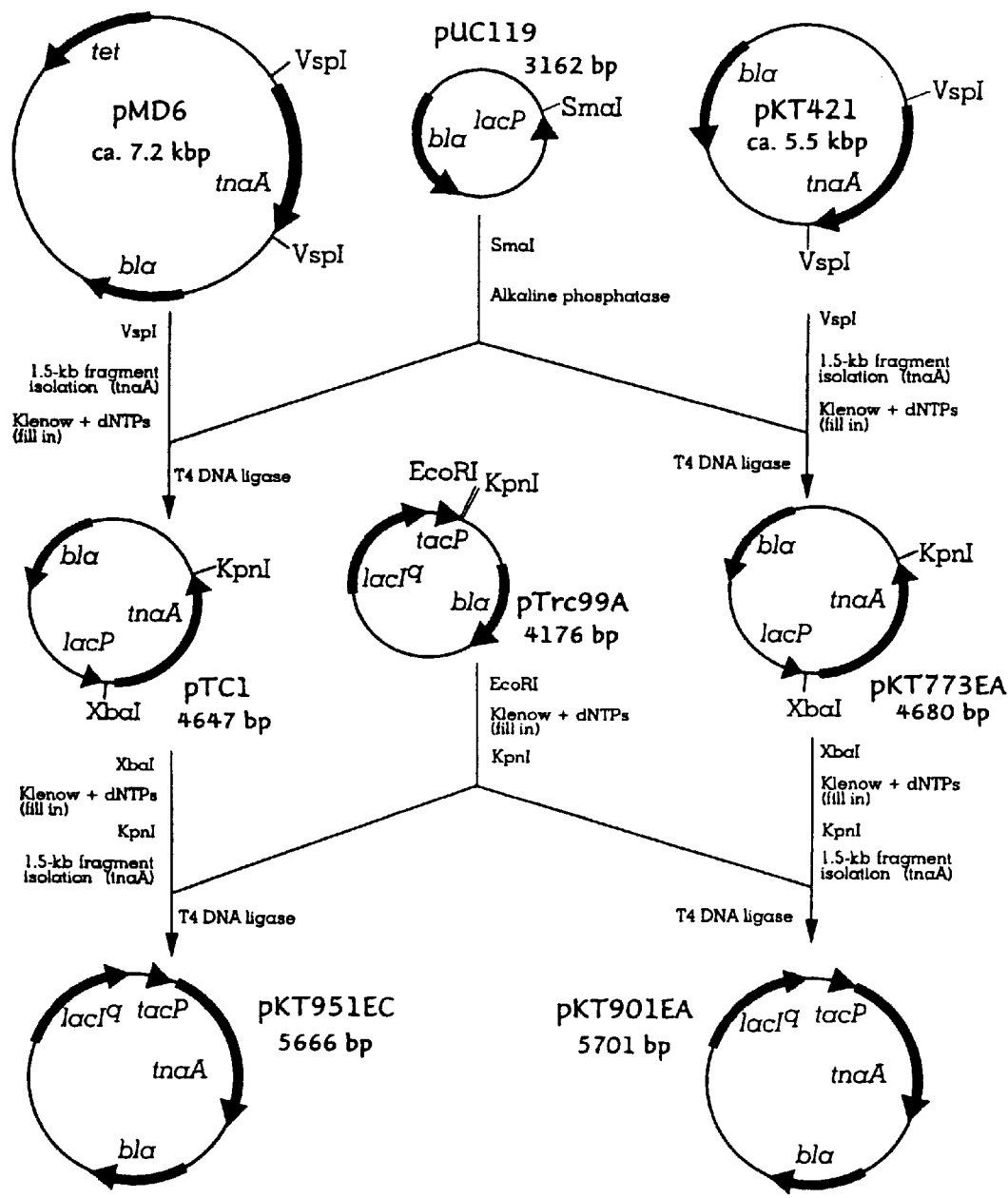
FIG. 1 shows a construction scheme of plasmids "pKT901EA" and "pKT951EC".

The tryptophanase used herein means an enzyme which catalyzes production of indole, ammonia, and pyruvic acid by acting on L-tryptophan.

In this invention, tryptophanase to be contacted with a mixture of D,L-tryptophan includes partially purified enzyme as well as purified enzyme.

The microorganisms producing tryptophanase used herein include animal cells and plant cells, which produce tryptophanase. The treated products used herein include these microorganisms that have been subjected to treatment with a surfactant, treatment with an organic solvent, mechanical treatment, enzymatic treatment, etc., to confer membrane permeability on the microorganisms, and the disrupted products of these microorganisms obtained by the above treatments.

Microorganisms producing tryptophanase used herein include Achromobacter, Aeromonas, Agrobacterium, Alcaligenes, Bacteroides, Cellulomonas, Clostridium, Citrobacter, Corynebacterium, Enterobacter, Erwinia, Escherichia, Fusobacterium (J. Gen. Microbiol. 86, 147–155 (1975)), Hansenula, Klebsiella, Kluyvera, Micrococcus, Morganella, Nocardia, Paenibacillus, Pantoea, Pasteurella, Peptostreptococcus, Pichia (JP-B-Sho 51-6235), Propionibacterium, Proteus, Providencia, Pseudomonas, Salmonella, Serratia, Sphaerophorus, Symbiobacterium, Vibrio, Xanthomonas, and so on.

Among these, particularly preferable microorganisms include *Achromobacter liquidum* (Appl. Environ. Microbiol. 46, 1–5 (1983)), OUT 8012 (stored in Osaka University); *Aeromonas hydrophila*, ATCC 14715 (which was classified as *Aeromonas liquefaciens* at the time of publication of the literature, J. Biol. Chem. 240, 1211–1218 (1965)); *Aeromonas hydrophila subsp. hydrophila*, IFO 3820, IFO 12658 (JP-A-Sho 60-34192); *Agrobacterium tumefasciens* (JP-B-Sho 51-6235), IFO 3058; *Alcaligenes faecalis* (J. Biotechnol. 5, 17–28 (1987)), OUT 8025 (stored in Osaka University), IFO 1311; *Bacteroides fragilis* (J. Natl. Cancer Inst. 54, 1073–1078 (1975)); *Cellulomonas sp.*, ATCC 490 (which was classified as *Pseudomonas perlurida* at the time of publication of the literature, JP-B-Sho 51-6235),; *Citrobacter freundii*, IFO 12681, ATCC 8090 (JP-B-Sho 51-6235), AHU 1534; *Clostridium felsineum*, ATCC 13160 (JP-B-Sho 51-6235); *Corynebacterium ammoniagenes*, IF012612; *Enterobacter aerogenes*, IFO 12010, SM-12 (Agri. Biol. Chem. 48, 2663–2668 (1984)); *Enterobacter cloacae*, ATCC 7256 (which was classified as *Aerobacter aerogenes* at the time of publication of the literature, JP-B-Sho 51-6235); *Fusobacterium varium*, ATCC 8501 (which was classified as *Sphaerophorus varius* at the time of publication of the literature, J. Bacteriol. 98, 167–171 (1969)); *Erwinia carotovora* (Aminosan-Kakusan (Amino acid-Nucleic acid) 27, 19–24 (1973)), *Erwinia carotovora subsp. carotovora*, IFO 12380; *Escherichia coli*, IFO 12713 (W3110),ATCC10798,ATCC3655 (JP-B-Sho51-6235); *Klebsiella oxytoca*, ATCC 8724 (which was classified as *Enterobacter aerogenes* at the time of publication of the literature, Aminosan-Kakusan (Amino acid-Nucleic acid) 27, 19–24 (1973)); *Klebsiella planticola*, ATCC 8329 (which was classified as *Enterobacter aerogenes* at the time of publication of the literature, Aminosan-Kakusan (Amino acid-Nucleic acid) 27, 19–24 (1973)); *Klebsiella pneumoniae*, IFO 3318; *Kluyvera ascorbata*, JCM 1681, ATCC 14236 (which was classified as *Kluyvera citrophila* at the time of publication of the literature, JP-B-Sho 51-6235); *Morganella morganii*, IFO 3168, *Morganella morganii subsp. morganii*, IFO 3848 (which was classified as *Proteus morganii* at the time of publication of the literature, Aminosan-Kakusan (Amino acid-Nucleic acid) 27, 19–24 (1973)); *Nocardia asteroides*, IFO 3384 (JP-B-Sho 51-6235); *Paenibacillus alvei*, IFO 3343; *Pantoea agglomerans*, ATCC 21433, ATCC 21434 (which was classified as *Erwinia herbicola* at the time of publication of the literature, JP-B-Sho 51-6235), FERM P-11349; *Pantoea ananas*, ATCC 23822 (*Erwinia herbicola* at the time of publication of the literature, Aminosan-Kakusan (Amino acid-Nucleic acid) 27, 19–24 (1973)); *Pasteurella multocida* (Bull. Univ. Osaka Prefect., Ser. B, 19, 31–41 (1967)), *Peptostreptococcus asaccharolyticus*, JCM 8143; *Pichia anomala*, IFO 0118 (JP-B-Sho 51-6235); *Propionibacterium acnes*, ATCC 6919 (which was classified as *Corynebacterium acnes* at the time of publication of the literature, J. Bacteriol. 98, 167–171 (1969)); *Proteus inconstans*, IFO 12931 (JP-B-Hei 03-47080); *Proteus mirabilis*, IFO 13300, ATCC 15290 (JP-B-Sho 51-6235); *Proteus vulgaris*, IFO 3167, *Providencia rettgeri*, ATCC 9919 (JP-A-Sho 63-52884); ATCC 29944 (JP-A-Hei 02-255082); *Pseudomonas putida*, IFO 14796; *Serratia grimesii*, ATCC 14460 (which was classified as *Aerobacter licheniformis* at the time of publication of the literature, JP-B-Sho 51-6235); *Salmonella choleraesuis subsp. choleraesuis* (which was classified as *Salmonella gallinarum* at the time of publication of the literature, JP-B-Sho 51-6235); *Sphaerophorus funduliformis* (Biochim. Biophys. Acta 386, 340–351 (1975)); *Symbiobacterium thermophilum*, IAM 13621 (Appl. Environ. Microbiol. 58, 2633–2642 (1992)), *Vibrio harveyi* (which was classified as *Photobacterium harveyi* at the time of publication of the literature, J. Bacteriol. 98, 167–171 (1969)), *Vibrio cholerae* (Acta Microbiol. Pol., Ser. A, 5, 75–79 (1973)), *Xanthomonas campestris* (JP-B-Sho 51-6235), *Xanthomonas campestris pv. oryzae*, IAM 1657, and so on.

In this invention, partially purified enzymes or purified enzymes can also be used. Purification of the enzymes from the above microorganisms, which are known to produce tryptophanase, can be carried out by the conventional methods, namely, an appropriate combination of salting out using ammonium sulfate, etc., ion exchange chromatography, hydrophobic chromatography, affinity chromatography, gel filtration, and the like. For example, the tryptophanase genes of *Aeromonas hydrophila,* ATCC 14715 (which was classified as *Aeromonas liquefaciens* at the time of publication of the literature, J. Biol. Chem. 240, 1211–1218 (1965)) and *Enterobacter aerogenes* were cloned and the tryptophanase can be purified easily from that produced by *Escherichia coli* in which the gene has been introduced and expressed (Biosci. Biotech. Biochem. 59, 1938–1943 (1995)). The enzymes can also be purified from those produced by *Escherichia coli* (J. Biol. Chem. 247, 1566–(1972)), *Morganella morganii subsp. morganii,* ATCC 23548 (which was classified as *Proteus morganii* at the time of publication of the literature, Can. J. Microbiol. 21, 828–833 (1975)), *Paenibacillus alvei* (which was classified as *Bacillus alvei* at the time of publication of the literature, J. Biol. Chem. 247, 1750–(1972)), *Sphaerophorus funduliformis* (Biochim. Biophys. Acta 386, 340–351 (1975)), *Symbiobacterium thermophilum* (Agri. Biol. Chem. 55, 3059–3066(1991)), *Vibrio sp.* (Arch. Microbiol. 122, 169–175(1979)), and the like by the methods as described in the respective literatures.

In addition, tryptophanase obtained from heterologous microorganisms in which the tryptophanase gene has been introduced, the heterologous microorganisms, or their treated products can be used. For example, the tryptophanase genes of *Alcaligenes faecalis* (J. Biotechnol. 5, 17–28 (1987)), *Enterobacter aerogenes* (J. Gen. Microbiol. 139, 3275–3281 (1993)), *Escherichia coli* (J. Bacteriol. 147, 787–796 (1981)), *Proteus inconstans* (JP-A-Hei 03-47080), *Proteus vulgaris* (J. Biol. Chem. 267, 19978–19985 (1992)), *Providencia rettgeri* (JP-A-Hei 02-255082), *Symbiobacterium thermophilum* (Appl. Environ.Microbiol. 58, 2633–2642 (1992)) were cloned and their nucleotide sequences were elucidated, and thus it is possible to introduce these genes into the host heterologous microorganisms, such as Aspergillus, Bacillus, Brevibacterium, Candida, Cephalosporium, Corynebacterium, *Escherichia coli*, Hansenula, Kluyveromyces, Lactobacillus, Neurospora, Pichia, Providencia, Pseudomonas, Rhodosporidium, Saccharomyces, Schizosaccharomyces, Serratia, Streptococcus, Trichosporon, Trichoderma, Yarrowia, Zygosaccharomyces, thereby allowing them to express tryptophanase. The tryptophanase gene can also be inserted into a vector in combination with appropriate promoter, expression regulatory factor, terminator, etc. to increase expression efficiency, and the resulting vector is introduced into the host for expression. Suitable expression vectors carrying the tryptophanase gene include pKT901EA, pKT951EC used in Examples, and the like.

For cultivation of tryptophanase-producing microorganisms, the usual culture medium containing the additives for increasing tryptophanase activity can be used. It is known, for example, that tryptophanase is an inducible enzyme in general and that the productivity of tryptophanase is increased by adding L-tryptophan in the culture medium. On the other hand, since L-tryptophan added as an inducer is metabolized by the action of tryptophanase to form indole, which generally inhibits growth of microorganisms, the growth inhibition by indole can be obviated by adding a surfactant, such as Sorpol W-200 (product of Toho Chemical Industry), in the culture medium (JP-B-Sho 51-6235). In the case that the gene coding for tryptophanase is expressed in heterologous microorganisms, it is desirable to apply culture and inducing methods suitable for the promoters used. For example, when a promoter, such as trc, lac, or tac, is used for expression in *Escherichia coli,* the tryptophanase activity can be increased by adding an inducer, such as lactose or IPTG (isopropylthiogalactopyranoside), from the beginning of cultivation or at an appropriate timing during cultivation.

A mixture of D, L-tryptophan may be contacted with tryptophanase, microorganisms producing tryptophanase, or their treated products, by any means that fulfils the conditions preferable for activity and stability of tryptophanase. Since ammonium ion, potassium ion, etc. generally activate tryptophanase, addition of these ions to the reaction medium is effective to enhance the activity. In addition, since tryptophanase is an enzyme that requires pyridoxal 5'-phosphate as coenzyme, pyridoxal 5'-phosphate can be effectively added to increase activity and stability. The pH of the reaction medium can be maintained preferably at such a value that tryptophanase can exhibit its activity, particularly at pH 7.0–9.5. For this contacting reaction, one of ordinary skill in the art would readily determine the optimal reaction conditions depending on the tryptophanase, the microorganisms, or treated product thereof to be used.

In the case that microorganisms producing tryptophanase are used for the reaction, it is possible to utilize the microbial cells which are exposed to a surfactant, heat treatment, pH treatment, an organic solvent, and the like, to improve their membrane permeability.

Indole, which results from metabolism of L-tryptophan by tryptophanase, is an inhibitor of tryptophanase and interferes the D-tryptophan synthesis reaction. Such inhibition of tryptophanase by indole can be obviated by maintaining a low concentration of indole in the reaction medium, thereby enhancing the D-tryptophan synthesis reaction. The indole concentration in the reaction medium can be kept low by, for example, adding a nonionic, cationic, anionic, or amphoteric surfactant, such as Sorpol W-200 (product of Toho Chemical Industry) or Nonion NS230 (product of Nippon Fat and Oil), adding an organic solvent which can dissolve indole well and is hardly miscible with water, such as toluene or hexane, or adding water-insoluble polymer capable of binding to indole, such as polyethylene, polypropylene, polyurethane, or Amberlite XAD-7 (product of Organo). The surfactant, the organic solvent, or the water-insoluble polymer is preferably added to the reaction medium to give a final concentration of 0.01–10% (w/v), 0.01–50% (v/v), and 0.1–50% (w/v), respectively.

Pyruvic acid resulting from metabolism of L-tryptophan by tryptophanase is also an inhibitor of tryptophanase and interferes the D-tryptophan synthesis reaction. Inhibition of tryptophanase by pyruvic acid can be suppressed by keeping the concentration of pyruvic acid in the reaction mixture low, thereby promoting the D-tryptophan synthesis reaction.

The concentration of pyruvic acid in the reaction medium can be kept low by degrading pyruvic acid chemically or degrading by microorganisms. Particularly, pyruvic acid can be efficiently degraded by adding to the reaction system a microorganism capable of degrading pyruvic acid but incapable of degrading D-tryptophan.

Preferable microorganisms capable of degrading pyruvic acid include, for example, microorganisms belonging to the genus Corynebacterium, Brevibacterium, and Saccharomyces.

In this invention, it is possible to utilize strains that are treated by artificial mutation, recombinant DNA, or the like techniques to be deficient in intracellular enzymes involved in degradation of D-tryptophan, including D-amino acid dehydrogenase, D-amino acid oxidase, D-amino acid transaminase, tryptophan 2,3-dioxygenase, D-amino acid acetyltransferase, amino acid racemase, and the like.

In this invention, although there is no particular restriction in the ratio of D-tryptophan to L-tryptophan in the D,L-tryptophan mixture that is contacted with tryptophanase, microorganisms producing tryptophanase, or their treated products, the content of L-tryptophan is preferably not more than 50%.

D-tryptophan thus produced can be recovered from the reaction mixture by the known methods. For example, the microbial cells can be separated by centrifugation, ultrafiltration, or the like method, followed by concentrating crystallization, cooling crystallization, neutralizing crystallization, or the like crystallization method. (JP-A-Sho 59-45897, JP-A-Sho 62-265254, JP-A-Hei 3-147794, etc.)

This invention enables the production of D-tryptophan with high optical purity and high yield.

This invention is described further in detail with reference to the following Examples, but is not to be construed to be restricted thereto.

EXAMPLE 1

Cultivation of Microorganisms Capable of Producing Tryptophanase

A 5 ml portion of bouillon medium (Nissui Pharmaceutical) was each inoculated with *Aeromonas hydrophila subsp. hydrophila* IFO 3820, *Agrobacterium tumefasciens* IFO 3058, *Alcaligenes faecalis* IFO 1311, *Cellulomonas sp.* ATCC 490, *Citrobacter freundii* IFO 12681, *Corynebacterium ammoniagenes* IFO 12612, *Enterobacter aerogenes* IFO 12010, *Erwinia carotovora Subsp. carotovora* IFO-12380, *Escherichia coli* IFO 12713, *Klebsiella pneumoniae* IFO 3318, *Kluyvera ascorbata* JCM 1681, *Morganella morganii* IFO 3168, *Paenibacillus alvei* IFO 3343, *Pantoea agglomerans* FERM P-11349, *Peptostreptococcus asaccharolyticus* JCM 8143, *Pichia anomala* IFO 0118, *Proteus mirabilis* IFO 13300, *Proteus vulgaris* IFO 3167, *Providencia rettgeri* ATCC 29944, *Pseudomonas putida* IFO 14796, *Serratia grimesii* ATCC 14460, *Xanthomonas campestris pv. oryzae* IAM 1657, and cultivated with shaking at 30° C. for 20 hours, each of which were then inoculated in 50 ml of tryptophanase producing medium (2 g of L-tryptophan, 5 g of potassium dihydrogenphosphate, 0.5 g of magnesium sulfate heptahydrate, 60 g of corn steep liquor, and 20 g of soybean protein hydrolysate in 1 L, pH 7.5) and cultured at 30° C. for 20 hours. The culture media obtained was each centrifuged to give the microbial cells containing tryptophanase.

EXAMPLE 2

Cultivation of Microorganisms Capable of Producing Tryptophanase

A 5 ml portion of YM medium was inoculated with *Pichia anomala* IFO 0118 and cultivated with shaking at 30° C. for 20 hours, which was inoculated in 50 ml of the tryptophanase production medium followed by cultivation at 30° C. for 20 hours. The resulting culture medium was centrifuged to give the microbial cells containing tryptophanase.

EXAMPLE 3

Cultivation of Recombinant Microorganism having Tryptophanase Gene

*Eshecherichia coli* JM109 strain carrying plasmid (pKT901EA, pKT951EC) was inoculated into LB medium containing 50 μg/ml of ampicillin and cultivated with shaking at 37° C. for 3 hours, which was inoculated into LB medium containing 50 μg/ml of ampicillin, 1 mM IPTG, 0.5 mM pyridoxine hydrochloride followed by cultivation with shaking 37° C. for 9 hours. The resulting culture medium was centrifuged to give the microbial cells containing tryptophanase. pKT901EA was constructed as follows (Biosci. Biotech. Biochem., 59, 1938–1943, (1995)). pKT421 containing tryptophanase gene derived from *Enterobactor aerogenes* SM-18 (J.Gen. Microbiol. 139, 3275–3281 (1993)) was digested with VspI and subcloned in pUC119, which was digested with XbaI. The digested product was ligated to trc promoter of pTrc99A. pKT951EC was constructed in the same manner as pKT901EA (FIG. 1) using pMD6 containing tryptophanase gene derived from *Escherichia coli* K-12 (J. Bacteriol. 147, 787–796 (1981)).

EXAMPLE 4

Production of D-Tryptophan by Microbial Cells Containing Tryptophanase

The microbial cells recovered from 10 ml of the culture medium obtained in Examples 1, 2, and 3 were suspended in 10 ml of the reaction medium (2.5 g/L D,L-tryptophan, 0.05 mM pyridoxal 5'-phosphate, 300 mM potassium phosphate buffer (pH 8.0)) and the reaction was carried out with shaking at 37° C. for 20 hours. The optical purity and amount of tryptophan after the reaction were determined with Crown Pak CR(+) (product of Daicel Chemical Industries, Ltd.) using perchloric acid solution (pH 2.0) as eluent at 40° C. The results of the reaction were shown in Table 1.

EXAMPLE 5

Production of D-Tryptophan by Culture of Microbial Cells Containing Tryptophanase To 9 ml of the culture medium obtained in Examples 1, 2 and 3 were added 1 ml of 1 M potassium phosphate buffer (pH 8.0), 0.025 g of D,L-tryptophan, 50 μl of 10 mM pyridoxal 5'-phosphate. The mixture was allowed to react with shaking at 37° C. for 20 hours. The optical purity and amount of tryptophan after the reaction were determined with Crown Pak CR(+) (product of Daicel Chemical Industries, Ltd.) using perchloric acid solution (pH 2.0) as eluent at 40° C. The results of the reaction were shown in Table 1. (In Table 1, data of *Cellulomonas sp., Corynebacterium ammoniagenes, Providencia rettgeri,* and *Serratia grimesii* were obtained in this Example.)

TABLE 1

| Strain | 2.5 g/L DL-Trp | | |
|---|---|---|---|
| | Reaction time | Optical purity | Recovery |
| *Aeromonas hydrophila* subsp. *hydrophila* IFO 3820 | 48 hrs. | 31.9% | 88.8% |
| *Agrobacterium tumefasciens* IFO 3058 | 48 hrs. | 99.9% | 51.5% |
| *Alcaligenes faecalis* IFO 1311 | 24 hrs. | 99.9% | 55.5% |
| *Cellulomonas sp.* ATCC490 | 48 hrs. | 98.4% | 102% |
| *Citrobacter freundii* IFO 12681 | 48 hrs. | 99.9% | 80.8% |
| *Corynebacterium ammoniagenes* IFO 12612 | 48 hrs. | 91.5% | 75.8% |
| *Enterobactor aerogenes* IFO 12010 | 24 hrs. | 71.4% | 96.0% |
| *Erwinia carotovora* subsp. *carotovora* IFO 12380 | 48 hrs. | 99.9% | 49.1% |
| *Escherichia coli* IFO 12713 | 24 hrs. | 99.9% | 72.9% |
| *Klebsiella pneumoniae* IFO 3318 | 24 hrs. | 99.9% | 66.7% |
| *Kluyvera ascorbata* JCM 1681 | 24 hrs. | 99.9% | 91.2% |
| *Morganella morganii* IFO 3168 | 24 hrs. | 99.9% | 56.1% |
| *Paenibacillus alvei* IFO 3343 | 48 hrs. | 27.8% | 85.1% |
| *Pantoea agglomerans* FERM P-11349 | 48 hrs. | 81.1% | 85.7% |
| *Peptostreptococcus asaccharolyticus* JIC 8143 | 48 hrs. | 99.9% | 81.8% |
| *Pichia anomala* IFO 0118 | 48 hrs. | 99.9% | 89.6% |
| *Proteus mirabilis* IFO 13300 | 24 hrs. | 99.9% | 79.4% |
| *Proteus vulgaris* IFO 3167 | 24 hrs. | 99.9% | 83.2% |
| *Providencia rettgeri* ATCC 29944 | 48 hrs. | 99.9% | 90.3% |
| *Pseudomonas putida* IFO 14796 | 48 hrs. | 26.9% | 64.0% |
| *Serratia grimesii* ATCC 14460 | 48 hrs. | 99.9% | 81.5% |
| *Xanthomonas campestris* pv. *oryzae* IAM 1657 | 48 hrs. | 99.9% | 33.1% |
| *Escherichia coli* JM109 (pKT901EA) | 48 hrs. | 99.9% | 93.3% |
| *Escherichia coli* JM109 (pKT951EC) | 24 hrs. | 99.1% | 102% |

EXAMPLE 6

Cultivation of Microorganism Capable of Degrading Pyruvic Acid

*Corynebacterium ammoniagenes* IFO 12612 was inoculated into 5 ml of bouillon medium and cultivated with shaking at 30° C. for 20 hours, which was inoculated in 5 ml of bouillon medium followed by cultivation at 30° C. for 20 hours. The resulting culture medium was centrifuged to give the microbial cells capable of degrading pyruvic acid.

EXAMPLE 7

Production of D-Tryptophan by Microbial Cells having Assimilability of Pyruvic Acid and Microbial Cells Containing Tryptophanase The microbial cells (listed in Table 2) recovered from 10 ml of the culture medium of the tryptophanase-producing microorganism obtained in Examples 1 and 3 and the microbial cells obtained from 10 ml of the culture medium of the pyruvic acid-degrading microorganism obtained in Example 6 were suspended in 10 ml of the reaction medium (0.24 g/10 ml D,L-tryptophan, 0.05 mM pyridoxal 5'-phosphate, 300 mM potassium phosphate buffer (pH 8.0)) and the reaction was carried out with shaking at 37° C. for 20 hours. The optical purity and amount of tryptophan after the reaction were determined with Crown Pak CR(+) (product of Daicel Chemical Industries, Ltd.) using perchloric acid solution (pH 2.0) as eluent at 40° C. The results of the reaction were shown in Table 2.

EXAMPLE 8

Production of D-Tryptophan by Microbial Cells Containing Tryptophanase in the Presence of Surfactant, Solvent, or Adsorbent Resin To 9 ml of the culture medium (listed in Table 2) obtained in Examples 1 and 3 were added 1 ml of 1 M potassium phosphate buffer (pH 8.0), 0.24 g of D,L-tryptophan, 50 µl of 10 mM pyridoxal 5'-phosphate, and any one of 5 ml of toluene, 5 ml of hexane, 500 µl of Sorpol W200, 500 µl of Nonion NS230, or 0.7 g of Amberlite XAD-7. The reaction was carried out with shaking at 37° C. for 20 hours. The optical purity and amount of tryptophan after the reaction were determined with Crown Pak CR(+) (product of Daicel Chemical Industries, Ltd.) using perchloric acid solution (pH 2.0) as eluent at 40° C. The results of the reaction were shown in Table 2.

TABLE 2

| | *E. coli* JM109 (pKT901EA) | | | *Morganella morganii* IFO 3168 | | | *Corynebacterium ammoniagenes* IFO 12612 | | |
|---|---|---|---|---|---|---|---|---|---|
| Additives | Reaction time | Optical purity | Recovery | Reaction time | Optical purity | Recovery | Reaction time | Optical purity | Recovery |
| Control | 48 hrs. | 7.5% | 93.8% | 24 hrs. | 31.1% | 79.8% | 48 hrs. | 3.30% | 98.2% |
| Organic solvent | | | | | | | | | |
| toluene 33% | 48 hrs. | 48.8% | 108% | — | — | — | — | — | — |
| hexane 33% | 48 hrs. | 15.5% | 101% | — | — | — | — | — | — |
| Surfactant | | | | | | | | | |
| Sorpol W200 5% | 46 hrs. | 46.6% | 88.8% | 24 hrs. | 99.9% | 79.9% | — | — | — |
| Nonion NS230 5% | 46 hrs. | 38.2% | 88.6% | 24 hrs. | 99.9% | 84.9% | — | — | — |

TABLE 2-continued

| | E. coli JM109 (pKT901EA) | | | Morganella morganii IFO 3168 | | | Corynebacterium ammoniagenes IFO 12612 | | |
|---|---|---|---|---|---|---|---|---|---|
| Additives | Reaction time | Optical purity | Recovery | Reaction time | Optical purity | Recovery | Reaction time | Optical purity | Recovery |
| Resin XAD-7 7% | 48 hrs. | 30.7% | 91.7% | 48 hrs. | 61.4% | 83.5% | — | — | — |
| +Corynebacterium ammoniagenes | 48 hrs. | 13.9% | 97.6% | 48 hrs. | 46.3% | 82.3% | — | — | — |

What is claimed is:

1. A method for producing D-tryptophan which comprises contacting a D,L-tryptophan mixture with tryptophanase, a microorganism producing tryptophanase, or a treated product of a microorganism producing tryptophanase to selectively degrade L-tryptophan, thereby increasing the content of D-tryptophan in the D,L-tryptophan mixture.

2. The method as claimed in claim 1, wherein said D,L-tryptophan mixture is contacted with tryptophanase derived from a microorganism belonging to the genus Aeromonas, Enterobacter, Escherichia, Morganella, Paenibacillus, Proteus, Sphaerophorus, Symbiobacterium, or Vibrio.

3. The method as claimed in claim 2, wherein said tryptophanase is derived from *Aeromonas hydrophila, Enterobacter aerogenes, Escherichia coli, Morganella morganii subsp. morganii, Paenibacillus alvei, Proteus vulgaris, Sphaerophorus funduliformis,* or *Symbiobacterium thermophilum.*

4. The method as claimed in claim 1, wherein said D,L-tryptophan mixture is contacted with a microorganism belonging to the genus Achromobacter, Aeromonas, Agrobacterium, Alcaligenes, Bacteroides, Cellulomonas, Citrobacter, Clostridium, Corynebacterium, Enterobacter, Erwinia, Escherichia, Fusobacterium, Klebsiella, Kluyvera, Morganella, Nocardia, Paenibacillus, Pantoea, Pasteurella, Peptostreptococcus, Pichia, Propionibacterium, Proteus, Providencia, Pseudomonas, Salmonella, Serratia, Sphaerophorus, Symbiobacterium, Vibrio, or Xanthomonas, or a treated product thereof.

5. The method as claimed in claim 4, wherein said microorganism is *Achromobacter liquidum, Aeromonas hydrophila, Aeromonas hydrophila subsp. hydrophila, Agrobacterium tumefasciens, Alcaligenes faecalis, Bacteroides fragilis, Citrobacter freundii, Clostridium felsineum, Corynebacterium ammoniagenes, Enterobacter aerogenes, Enterobacter cloacae, Erwinia carotovora, Escherichia coli, Fusobacterium varium, Klebsiella oxytoca, Klebsiella planticola, Klebsiella pneumoniae, Kluyvera ascorbata, Morganella morganii subsp. morganii, Nocardia asteroides, Paenibacillus alvei, Pantoea agglomerans, Pantoea ananas, Pasteurella multocida, Peptostreptococcus asaccharolyticus, Pichia anomala, Propionibacterium acnes, Proteus inconstans, Proteus mirabilis, Proteus vulgaris, Providencia rettgeri, Pseudomonas putida, Salmonella choleraesuis subsp. choleraesuis, Serratia grimesii, Sphaerophorus funduliformis, Symbiobacterium thermophilum, Vibrio harveyi, Vibrio cholerae,* or *Xanthomonas campestris.*

6. The method as claimed in claim 1, wherein said D,L-tryptophan mixture is contacted with transformants in which a tryptophanase gene has been introduced, or their treated products.

7. The method as claimed in claim 6, wherein said tryptophanase gene is derived from a microorganism belonging to the genus Alcaligenes, Enterobacter, Escherichia, Proteus, Providencia, or Symbiobacterium.

8. The method as claimed in claim 7, wherein said tryptophanase gene is derived from *Alcaligenes faecalis, Enterobacter aerogenes, Escherichia coli, Proteus inconstans, Proteus Vulgaris, Providencia rettgeri,* or *Symbiobacterium thermophilum.*

9. The method as claimed in claim 2, wherein a microorganism grown in a culture medium containing L-tryptophan is used.

10. The method as claimed in claim 4, wherein a microorganism grown in a culture medium containing L-tryptophan is used.

11. The method as claimed in claim 6, wherein a microorganism grown in a culture medium containing L-tryptophan is used.

12. The method as claimed in claim 1, which further comprises adding to a reaction mixture a surfactant, a nonaqueous solvent which dissolves indole easily, or a water-insoluble resin capable of binding to indole.

13. The method as claimed in claim 12, wherein said surfactant is Sorpol W-200 or Nonion NS230, said resin capable of binding to indole is Amberlite XAD-7, and the organic solvent is toluene or hexane.

14. The method as claimed in claim 1, which further comprises adding to the reaction mixture a microorganism capable of degrading pyruvic acid.

15. The method as claimed in claim 14, wherein said microorganism capable of degrading pyruvic acid is a microorganism belonging to the genus Corynebacterium.

* * * * *